United States Patent [19]

Berkoff et al.

[11] 3,962,438

[45] June 8, 1976

[54] ANTI-ARTHRITIC 1H-PYRIMIDO-(5,4,3-KL)PHENOTHIAZINE-1,3(2H)-DIONES AND 1-THIONES

[75] Inventors: Charles E. Berkoff, Huntingdon Valley; Blaine M. Sutton, Hatboro; Joseph Weinstock, Phoenixville, all of Pa.

[73] Assignee: SmithKline Corporation, Philadelphia, Pa.

[22] Filed: Jan. 7, 1975

[21] Appl. No.: 539,208

[52] U.S. Cl............................ 424/247; 260/243 A
[51] Int. Cl.² ............... A61K 27/00; C07D 513/22
[58] Field of Search................ 260/243 A; 424/247

[56] References Cited
UNITED STATES PATENTS
3,493,567   2/1970   Draper et al.................... 260/243 A

*Primary Examiner*—Henry R. Jiles
*Assistant Examiner*—R. W. Ramsuer
*Attorney, Agent, or Firm*—Janice E. Williams; William H. Edgerton

[57] ABSTRACT

1H-Pyrimido[5,4,3-kl]phenothiazine-1,3(2H)-diones are prepared from the corresponding 1-thione-3-one compounds by methylation followed by acid hydrolysis. The 1,3-dione products and 1-thione-3-one intermediates are useful as anti-arthritic agents.

12 Claims, No Drawings

ANTI-ARTHRITIC 1H-PYRIMIDO-(5,4,3-KL)PHENOTHIAZINE-1,3(2H)-DIONES AND 1-THIONES

This invention relates to novel 1H-pyrimido [5,4,3-kl]phenothiazine-1,3(2H)-diones and 1-thione intermediates for the preparation thereof which have useful pharmacological activity. More specifically, the compounds of this invention have anti-arthritic activity as measured by their ability to inhibit adjuvant-induced polyarthritis in rats.

The compounds of this invention are represented by the following structural formula:

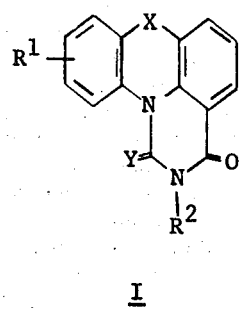

I in which:
X is S, SO or $SO_2$;
Y is O or S;
$R^1$ is hydrogen, halogen, lower alkyl, lower alkoxy, trifluoromethyl or nitro: and
$R^2$ is hydrogen, lower alkyl, hydroxy(lower)alkyl, dihydroxy(lower)alkyl or phenyl(lower)alkyl.

In the nomenclature used herein the pyrimido[5,4,3-kl]phenothiazine ring is numbered as follows:

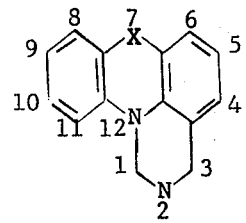

The terms "lower alkyl" and "lower alkoxy" refer to groups having from one to four carbon atoms.

Preferred compounds of this invention are represented by formula I in which $R^1$ is in the 10-position, Y is O and $R^2$ is hydrogen, lower alkyl or hydroxy(lower)alkyl.

Advantageous compounds are those where $R^1$ is trifluoromethyl in the 10-position, Y is O, X is SO or $SO_2$ and $R^2$ is hydrogen, lower alkyl, or hydroxy(lower)alkyl.

Particularly preferred are the compounds 2-(2-hydroxyethyl)-10-trifluoromethyl-1H-pyrimido[5,4,3-kl]phenothiazine-1,3(2H)-dione-7-oxide, 2-(2-hydroxyethyl)-10-trifluoromethyl-1H-pyrimido[5,4,3-kl]phenothiazine-1,3(2H)-dione-7,7-dioxide, 2-ethyl-10-trifluoromethyl-1H-pyrimido[5,4,3-kl]phenothiazine-1,3(2H)-dione-7-oxide, 10-trifluoromethyl-1H-pyrimido[5,4,3-kl]phenothiazine-1,3(2H)-dione-7,7-dioxide and 10-trifluoromethyl-1H-pyrimido[5,4,3-kl]phenothiazine-1,3(2H)-dione-7-oxide.

The compounds of formula I where X is S are prepared from the corresponding phenothiazine-1-carboxylic acids as shown in the following scheme:

SCHEME 1

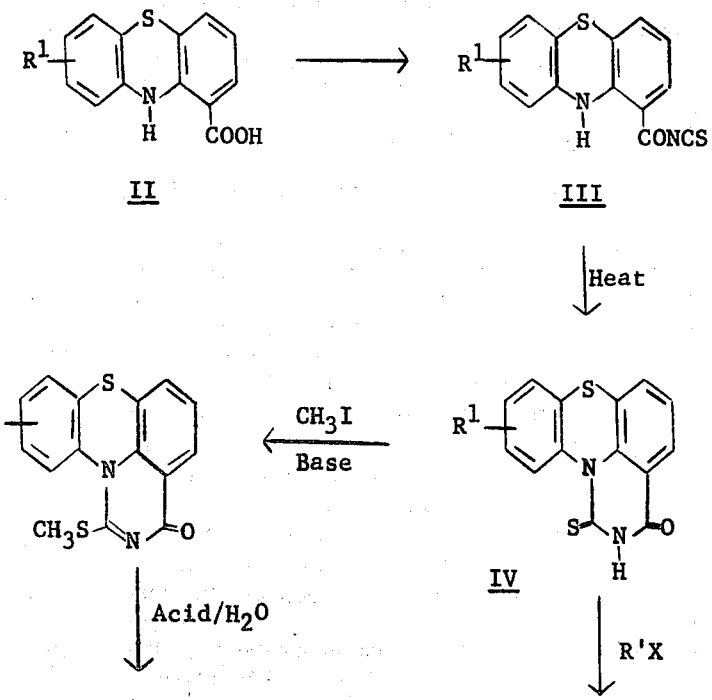

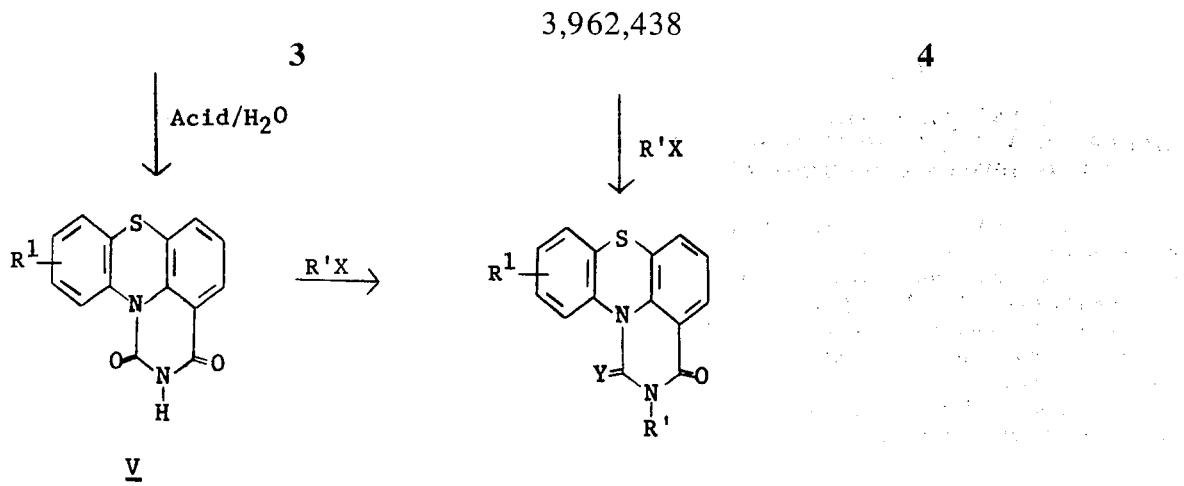

in which R¹ and Y are defined as above, R' is lower alkyl, hydroxy(lower)alkyl, dihydroxy(lower)alkyl, phenyl(lower)alkyl or diacetoxy(lower)alkyl and X is halogen, preferably chloro or bromo.

Thus, a phenothiazine-1-carboxylic acid of formula II is converted to the corresponding isothiocyanate III according to standard procedures, for example by reaction of the carboxylic acid chloride with an alkali metal thiocyanate such as potassium thiocyanate. Thermal cyclization of III gives a pyrimido phenothiazine-3-one-1-thione of formula IV. Treatment of IV with methyl iodide and a base such as sodium or potassium hydroxide followed by acid hydrolysis of the 1-methylmercapto derivative of IV gives a pyrimido phenothiazine-1,3-dione of formula V. Alkylation of IV or V with R'X in the presence of a strong base such as sodium or potassium hydride gives the N-alkylated compounds of formula I. When R' is dihydroxy(lower)alkyl and X is S, the compounds of formula I are preferably prepared by alkylation with a diacetoxyalkyl halide alkylating agent, such as 3-chloro-1,2-diacetoxypropane, with subsequent removal of the acetoxy groups, for example by heating in acid solution.

When X is SO, the corresponding compounds of formula I are prepared by oxidation of the compounds of formula I where X is S with m-chloroperbenzoic acid in, for example, cold methanol. Oxidation of the compounds of formula I where X is S with hydrogen peroxide in acetic acid gives the compounds of formula I where X is $SO_2$.

The starting phenothiazine-1-carboxylic acids of formula II are either known to the art or are prepared from reaction of an o-aminobenzenethiol and a 2-halo-3-nitrobenzoic acid as described in U.S. Pat. No. 3,519,622.

The anti-arthritic activity of the compounds of this invention is measured by their ability to inhibit adjuvant-induced polyarthritis in rats. The compounds of formula I produce marked inhibition of the development of adjuvant arthritis in rats at daily oral doses as low as about 50 mg. per kilogram of body weight.

Adjuvant arthritis in rats is produced by a single injection of 0.75 mg. of Mycobacterium butyricum suspended in white paraffin (N.F.) into a hindpaw (left footpad). The injected leg becomes inflamed and reaches a maximum volume in 3 to 5 days (primary lesion). The animals exhibit a decrease in body weight gain during this initial period. Adjuvant arthritis (secondary phase) occurs after a delay of approximately 10 days and is characterized by inflammation of the non-injected sites (right hind leg), decrease in body weight gain and further increases in the volume of the injected hing leg. The compounds of formula I administered in the doses described above beginning on the day of adjuvant injection and continuing for 17 days thereafter, exclusive of days 4, 5, 11 and 12, protect the animals against development of both primary and secondary lesions of adjuvant arthritis.

Pharmaceutical compositions having anti-arthritic activity which comprise a pharmaceutical carrier and a compound of formula I and methods of treating arthritis by administering internally to an animal an amount of a compound of formula I sufficient to inhibit arthritis are also objects of this invention.

The compounds of this invention are administered in conventional dosage unit forms by incorporating an amount sufficient to inhibit arthritis, without toxic effects, with a nontoxic pharmaceutical carrier according to accepted procedures. Preferably each dosage unit will contain the active medicament in an amount of from about 10 mg. to about 150 mg., preferably 25 mg. to 100 mg., per unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to the desired end product.

The method of treating arthritis in accordance with this invention comprises administering internally to an animal subject a compound of formula I, usually combined with a pharmaceutical carrier, in an amount sufficient to inhibit arthritis without limiting side effects. The active medicament will be administered in a dosage unit, as described above, orally or parenterally, the oral route being preferred. Advantageously, equal doses will be administered two or three times daily with the daily dosage regimen being from about 20 mg. to about 450 mg., preferably 50 mg. to about 300 mg. When the method described above is carried out, arthritis is inhibited with a minimum of side effects.

One skilled in the art will recognize that in determining the amounts of the compound needed to produce the desired pharmacological effect without toxic side effects, the activity of the compound as well as the size of the host animal must be considered.

The following examples illustrate the preparation of compounds of this invention and their incorporation into pharmaceutical compositions, and as such are not to be construed as limiting the invention set forth in the claims appended hereto. Temperatures are in degrees Centigrade unless otherwise stated.

EXAMPLE 1

10-Trifluoromethyl-1H-pyrimido[5,4,3-kl]phenothiazine-3-one-1(2H)-thione

8-Trifluoromethylphenothiazine-1-carboxylic acid (62.2 g., 0.20 mol.) was added to a stirred mixture of 300 ml. of chloroform and 300 ml. of phosphorus trichloride. The resulting brown suspension was cooled in an ice-bath while 50 ml. of dimethylformamide was added slowly until a reddish brown solution formed. After stirring the mixture for 4 hours at 25°, the chloroform and excess phosphorus trichloride were evaporated under reduced pressure. The resulting reddish brown solid residue was dissolved in 1500 ml. of boiling n-hexane. The hot, clear, reddish solution was decanted from a viscous, insoluble material and, on cooling, large red needles formed. The solid was collected by filtration and washed with hexane to give 8-trifluoromethylphenothiazine-1-carboxylic acid chloride, m.p. 124°–126°.

A solution of 56.5 g. (0.172 mol.) of 8-trifluoromethylphenothiazine-1-carboxylic acid chloride in 450 ml. of acetone was added over a 15 minute period to a stirred solution of 25.0 g. (0.257 mol.) of potassium thiocyanate in 200 ml. of acetone. The resulting reddish brown suspension was stirred at 25° for 1.5 hours. The reaction mixture was concentrated under reduced pressure to approximately 300 ml. then diluted with 700 ml. of water. The product was collected by filtration and washed thoroughly with water to give 8-trifluoromethylphenothiazine-1-carboxylic acid isothiocyanate, m.p. 145°–150°.

A slurry of 53.7 g. (0.168 mol.) of 8-trifluoromethylphenothiazine-1-carboxylic acid isothiocyanate in 30 ml. of diphenyl ether was heated in an oil bath at 210° for one hour. The reaction mixture first became a homogenous liquid and then turned into a solid mass. The cooled reaction mixture was refluxed for several minutes in 100 ml. of toluene, cooled to ambient temperature, and the insoluble material was collected by filtration and washed with several small portions of toluene to give the title compound, m.p. 297°–299° (ethanol).

EXAMPLE 2

10-Trifluoromethyl-1H-pyrimido[5,4,3-kl]phenothiazine-1,3-(2H)-dione

10-Trifluoromethyl-1H-pyrimido[5,4,3-kl]phenothiazine-3-one-1(2H)-thione (53.6 g., 0.152 mol.) was added to a stirred solution of 8.95 g. (0.160 mol.) of potassium hydroxide in 1680 ml. of acetone and 720 ml. of water. After all the solid had dissolved and a clear yellow solution formed, 22.8 g. (10 ml., 0.160 mol.) of methyl iodide was added in one portion. The reaction mixture was stirred at 25° for 18 hours, diluted with 1000 ml. of water and chilled in an ice-bath for several hours. The resulting light yellow solid was collected by filtration and washed with water to give 1-methylmercapto-10-trifluoromethyl-3H-pyrimido[5,4,3-kl]phenothiazine-3-one, m.p. 229°–231° (ethanol).

A stirred suspension of 53.6 g. (0.146 mol.) of 1-methylmercapto-10-trifluoromethyl-3H-pyrimido[5,4,3-kl]phenothiazine-3-one in 240 ml. of concentrated hydrochloric acid and 800 ml. of ethanol was heated under reflux for four hours. The reaction mixture was concentrated to approximately one-half its original volume by boiling off the excess solvents and chilled. The product was collected by filtration and washed thoroughly with water to give the title compound, m.p. 278°–280° (ethanol).

EXAMPLE 3

2-Ethyl-10-trifluoromethyl-1H-pyrimido[5,4,3-kl]phenothiazine-1,3(2H)-dione

57% Sodium hydride in mineral oil (4.2 g., 0.100 mol.) was added to a stirred solution of 28.0 g. (0.0834 mol.) of 10-trifluoromethyl-1H-pyrimido[5,4,3-kl]phenothiazine -1,3(2H)-dione in 220 ml. of dry dimethylformamide. The mixture was stirred for 1 hour at 25°, then 16.8 g. (8.6 ml., 0.108 mol.) of ethyl iodide was added. The resulting greenish yellow, turbid mixture was stirred for 4.5 hours at 25°, then filtered to give a clear yellow solution. The filtrate was evaporated to dryness under reduced pressure and the residue was triturated with petroleum ether to remove the mineral oil. The crude solid product was precipitated from a methanol-water mixture to give the title compound, m.p. 150°–152° (ethanol).

EXAMPLE 4

2-(2-Hydroxyethyl)-10-trifluoromethyl-1H-pyrimido[5,4,3-kl]phenothiazine-1,3(2H)-dione 57% Sodium hydride in mineral oil (8.4 g., 0.200 mol.) was added to a stirred solution of 28.0 g (0.0834 mol.) of 10-trifluoromethyl-1H-pyrimido[5,4,3-kl]phenothiazine -1,3(2H)-dione in 220 ml. of dry dimethylformamide. The mixture was stirred for 1 hour at 25°, then 54.0 g. (0.432 mol.) of 2-bromoethanol was added. The resulting mixture was stirred for 4.5 hours at 25°, then filtered. The filtrate was evaporated to dryness under reduced pressure and the residue was chromatographed on silica gel with chloroform and 90% chloroform-methanol as eluants to give the title compound, m.p. 90°–93° (methanol).

EXAMPLE 5

2-(2,3-Dihydroxypropyl)-10-trifluoromethyl-1H-pyrimido[5,4,-3-kl]phenothiazine-1,3(2H)-dione 3-Chloro-1,2-dihydroxypropane (55.2 g., 0.5 mol.) was treated with 90 g. of acetyl chloride with cooling (ice bath). The reaction mixture was then heated on a steam bath to 80°. Vacuum distillation gave 3-chloro-1,2-diacetoxypropane.

A mixture of 21.8 g. (0.112 mol.) of 3-chloro-1,2-diacetoxypropane, 28.0 g. (0.083 mol.) of 10-trifluoromethyl-1H-pyrimido[5,4,3-kl]phenothiazine-1,3(2H)-dione and 3.36 g. (0.080 mol.) of sodium hydride in 200 ml. of dry dimethylformamide was heated at 100°–110° for 40 hours in the presence of a catalytic amount of potassium iodide. The reaction mixture was filtered and the filtrate was evaporated to dryness under reduced pressure to give 2-(2,3- diacetoxypropyl)-10-trifluoromethyl-1H-pyrimido[5,4,3-kl]phenothiazine-1,3(2H)-dione.

A mixture of 48.1 g. (0.0975 mol.) of 2-(2,3-diacetoxypropyl)-10-trifluoromethyl-1H-pyrimido[5,4,3-kl]phenothiazine-1,3(2H)-dione in 200 ml. of methanol and 25 ml. of concentrated hydrochloric acid was heated under reflux for 0.5 hour, then allowed to stand overnight at ambient temperature. The white solid that precipitated was isolated by filtration and washed with water to give the title compound, m.p. 159°–162° (chloroform).

EXAMPLE 6

10-Trifluoromethyl-1H-pyrimido[5,4,3-kl]phenothiazine-1,3(2H)-dione-7-oxide m-Chloroperbenzoic acid (1.9 g., 0.011 mol.) was added portion-wise to a cold (0-5°), stirred solution of 3.36 g. (0.01 mol.) of 10-trifluoromethyl-1H-pyrimido[5,4,3-kl]phenothiazine-1,3(2H)-dione in 35 ml. of absolute methanol. The reaction mixture was stirred in the cold for one hour, then an additional four hours at ambient temperature. The reaction mixture was chilled and the precipitated product was collected by filtration and washed with ice-cold methanol to give the title compound, m.p. 302-304° (methanol).

EXAMPLE 7

10-Trifluoromethyl-1H-pyrimido[5,4,3-kl]phenothiazine-3-one-1(2H)-thione-7-oxide When an equivalent amount of 10-trifluoromethyl-1H-pyrimido[5,4,3-kl]phenothiazine-3-one-1(2H)-thione is substituted in the procedure of Example 6 for 10-trifluoromethyl-1H-pyrimido[5,4,3-kl]phenothiazine-1,3(2H)-dione, the title compound is obtained.

EXAMPLE 8

2-Ethyl-10-trifluoromethyl-1H-pyrimido[5,4,3-kl]phenothiazine-1,3(2H)-dione-7-oxide Substitution of an equivalent amount of 2-ethyl10-trifluoromethyl-1H-pyrimido[5,4,3-kl]phenothiazine-1,3(2H)-dione in the procedure of Example 6 for 10-trifluoromethyl-1H-pyrimido[5,4,3-kl]phenothiazine-1,3(2H)-dione gave the title compound, m.p. 184-186° (methanol).

EXAMPLE 9

2-(2-Hydroxyethyl)-10-trifluoromethyl-1H-pyrimido[5,4,3-kl]phenothiazine-1,3(2H)-dione-7-oxide When 2-(2-hydroxyethyl)-10-trifluoromethyl-1H-pyrimido[5,4,3-kl]phenothiazine-1,3(2H)-dione was oxidized with m-chloroperbenzoic acid as described in the procedure of Example 6, the title compound was obtained, m.p. 205-206° (ethanol).

EXAMPLE 10

2-(2,3-Dihydroxypropyl)-10-trifluoromethyl-1H-pyrimido[5,4,3-kl]phenothiazine-1,3(2H)-dione-7-oxide Reaction of 2-(2,3-dihydroxypropyl)-10-trifluoromethyl-1H-pyrimido[5,4,3-kl]phenothiazine-1,3(2H)-dione and m-chloroperbenozic acid according to the procedure of Example 6 gave the title compound, m.p. 224°–225° (chloroform-methanol).

EXAMPLE 11

10-Trifluoromethyl-1H-pyrimido[5,4,3-kl]phenothiazine-1,3(2H)-dione-7,7-dioxide

A mixture of 3.36 g. (0.01 mol.) of 10-trifluoromethyl-1H-pyrimido[5,4,3-kl]phenothiazine-1,3(2H)-dione and three equivalents of 30% hydrogen perioxide in 70 ml. of glacial acetic acid was heated at 75°–85° for 4 hours. The reaction mixture was cooled and diluted with water. The precipitated product was collected by filtration and washed with water to give the title compound, m.p. 290 –293° (methanol).

EXAMPLE 12

10-Trifluoromethyl-1H-pyrimido[5,4,3-kl]phenothiazine-3-one-1(2H)-thione-7,7-dioxide When an equivalent amount of 10-trifluoromethyl-1H-pyrimido[5,4,3-kl]phenothiazine-3-one-1(2H)-thione is substituted in the procedure of Example 11 for 10-trifluoromethyl-1H-pyrimido[5,4,3-kl]phenothiazine-1,3(2H)-dione, the title compound is obtained.

EXAMPLE 13

2-Ethyl-10-trifluoromethyl-1H-pyrimido[5,4,3-kl]phenothiazine-1,3(2H)-dione-7,7-dioxide Substitution of an equivalent amount of 2ethyl10-trifluoromethyl-1H-pyrimido[5,4,3-kl]phenothiazine-1,3(2H)-dione in the procedure of Example 11 for 10-trifluoromethyl-1H-pyrimido[5,4,3-kl]phenothiazine-1,3(2H)-dione gave the title compound, m.p. 208°–210° (methanol).

EXAMPLE 14

2-(2-Hydroxyethyl)-10-trifluoromethyl-1H-pyrimido[5,4,3,-kl]phenothiazine-1,3(2H)-dione-7,7-dioxide When 2-(2-hydroxyethyl)-10-trifluoromethyl-1H-pyrimido[5,4,3-kl]phenothiazine-1,3(2H)-dione was oxidized with hydrogen peroxide as described in the procedure of Example 11, the title compound was obtained, m.p. 189°–192° (1-chlorobutane).

EXAMPLE 15

2-(2,3-Dihydroxypropyl)-10-trifluoromethyl-1H-pyrimido[5,4,3-kl]phenothiazine-1,3(2H)-dione-7,7-dioxide Reaction of 2-(2,3dihydroxypropyl)-10-trifluoromethyl-1H-pyrimido[5,4,3-kl]phenothiazine-1,3(2H)-dione and hydrogen peroxide according to the procedure of Example 11 gave the title compound, m.p. 223°–226° (1-chlorobutanemethanol).

EXAMPLE 16

When a phenothiazine-1-carboxylic acid listed below:
  phenothiazine-1-carboxylic acid
  8-chlorophenothiazine-1-carboxylic acid
  8-fluorophenothiazine-1-carboxylic acid
  9-methylphenothiazine-1-carboxylic acid
  7-methoxyphenothiazine-1-carboxylic acid
  9-trifluoromethylphenothiazine-1-carboxylic acid
  7-trifluoromethylphenothiazine-1-carboxylic acid
is used as a starting material in the procedure of Example 1 in place of 8-trifluoromethylphenothiazine-1-carboxylic acid, the following pyrimido[5,4,3-kl]phenothiazine-3-one-1(2H)-thiones are obtained as final products:

1H-pyrimido[5,4,3-kl]phenothiazine-3-one-1(2H)-thione 10-chloro-1H-pyrimido[5,4,3-kl]phenothiazine-3-one-1(2H)-thione 10-fluoro-1H-pyrimido[5,4,3-kl]phenothiazine-3-one-1(2H)-thione 11-methyl-1H-pyrimido[5,4,3-kl]phenothiazine-3-one-1(2H)-thione 9-methoxy-1H-pyrimido[5,4,3-kl]phenothiazine-3-one-1(2H)-thione 11-trifluoromethyl-1H-pyrimido[5,4,3-kl]phenothiazine-3-one-1(2H)-thione 9-trifluoromethyl-1H-pyrimido[5,4,3-kl]phenothiazine-3-one-1(2H)-thione.

EXAMPLE 17

Use of a pyrimido[5,4,3-kl]phenothiazine-3-one-1(2H)-thione listed in Example 16 as a starting material in the procedure of Example 2 followed by acid hydrolysis of the 1-methylmercapto derivative as described therein gives the compounds listed below as final products:

1H-pyrimido[5,4,3-kl]phenothiazine-1,3(2H)-dione 10-chloro-1H-pyrimido[5,4,3-kl]phenothiazine-1,3-(2H)-dione 10-fluoro-1H-pyrimido[5,4,3-kl]phenothiazine-1,3-(2H)-dione 11-methyl-1H-pyrimido[5,4,3-kl]phenothiazine-1,3-(2H)-dione 9-methoxy-1H-pyrimido[5,4,3-kl]phenothiazine-1,3-(2H)-dione 11-trifluoromethyl-1H-pyrimido[5,4,3-kl]phenothiazine-1,3(2H)-dione 9-trifluoromethyl-1H-pyrimido[5,4,3-kl]phenothiazine-1,3(2H)-dione.

EXAMPLE 18

Substitution of a pyrimido[5,4,3-kl]phenothiazine-1,3(2H)-dione from Example 17 in the procedure of Example 4 in place of 10-trifluoromethyl-1H-pyrimido[5,4,3-kl]phenothiazine-1,3(2H)-dione gives the following compounds of this invention, respectively:

2-(2-hydroxyethyl)-1H-pyrimido[5,4,3-kl]phenothiazine-1,3(2H)-dione 10-chloro-2-(2-hydroxyethyl)-1H-pyrimido[5,4,3-kl]phenothiazine-1,3(2H)-dione 10-fluoro-2-(2-hydroxyethyl)-1H-pyrimido[5,4,3-kl]phenothiazine-1,3(2H)-dione 2-(2-hydroxyethyl)-11-methyl-1H-pyrimido[5,4,3-kl]phenothiazine-1,3(2H)-dione 2-(2-hydroxyethyl)-9-methoxy-1H-pyrimido[5,4,3-kl]phenothiazine-1,3(2H)-dione 2-(2-hydroxyethyl)-11-trifluoromethyl-1H-pyrimido[5,4,3-kl]phenothiazine-1,3(2H)-dione 2-(2-hydroxyethyl)-9-trifluoromethyl-1H-pyrimido[5,4,3-kl]phenothiazine-1,3(2H)-dione.

Similarly, the pyrimido[5,4,3-kl]phenothiazine-1,3(2H)-diones and pyrimido[5,4,3-kl]phenothiazine-3-one-1(2H)-thiones disclosed herein may be alkylated with the other alkylating agents described herein according to procedures described above.

EXAMPLE 19

Oxidation of a pyrimido[5,4,3-kl]phenothiazine-1,3(2H)-dione from Example 18 with m-chloroperbenzoic acid as described in the procedure of Example 6 gives the following compounds of this invention:

2-(2-hydroxyethyl)-1H-pyrimido[5,4,3-kl]phenothiazine-1,3(2H)-dione-7-oxide 10-chloro-2-(2-hydroxyethyl)-1H-pyrimido[5,4,3-kl]phenothiazine-1,3(2H)-dione-7-oxide 10-fluoro-2-(2-hydroxyethyl)-1H-pyrimido[5,4,3-kl]phenothiazine-1,3(2H)-dione-7-oxide 2-(2-hydroxyethyl)-11-methyl-1H-pyrimido[5,4,3-kl]phenothiazine-1,3(2H)-dione-7-oxide 2-(2-hydroxyethyl)-9-methoxy-1H-pyrimido[5,4,3-kl]phenothiazine-1,3(2H)-dione-7-oxide 2-(2-hydroxyethyl)-11-trifluoromethyl-1H-pyrimido[5,4,3-kl]phenothiazine-1,3(2H)-dione-7-oxide 2-(2-hydroxyethyl)-9-trifluoromethyl-1H-pyrimido[5,4,3-kl]phenothiazine-1,3(2H)-dione-7-oxide.

By similar procedures, the other pyrimido[5,4,3-kl]phenothiazine-1,3(2H)-diones and pyrimido[5,4,3-kl]phenothiazine-3-one-1(2H)-thiones disclosed herein may be oxidized to the corresponding 7-oxide compounds.

EXAMPLE 20

Oxidation of a pyrimido[5,4,3-kl]phenothiazine-1,3(2H)-dione from Example 18 with hydrogen peroxide in acetic acid as described in the procedure of Example 11 gives the following compounds of this invention:

2-(2-hydroxyethyl)-1H-pyrimido[5,4,3-kl]phenothiazine-1,3(2H)-dione-7,7-dioxide 10-chloro-2-(2-hydroxyethyl)-1H-pyrimido[5,4,3-kl]phenothiazine-1,3(2H)-dione-7,7-dioxide 10-fluoro-2-(2-hydroxyethyl)-1H-pyrimido[5,4,3-kl]phenothiazine-1,3(2H)-dione-7,7-dioxide 2-(2-hydroxyethyl)-11-methyl-1H-pyrimido[5,4,3-kl]phenothiazine-1,3(2H)-dione-7,7-dioxide 2-(2-hydroxyethyl)-9-methoxy-1H-pyrimido[5,4,3-kl]phenothiazine-1,3(2H)-dione-7,7-dioxide 2-(2-hydroxyethyl)-11-trifluoromethyl-1H-pyrimido[5,4,3-kl]phenothiazine-1,3(2H)-dione-7,7-dioxide 2-(2-hydroxyethyl)-9-trifluoromethyl-1H-pyrimido[5,4,3-kl]phenothiazine-1,3(2H)-dione-7,7-dioxide.

By similar procedures, the other pyrimido[5,4,3-kl]phenothiazine-1,3(2H)-diones and pyrimido[5,4,3-kl]-phenothiazine-3-one-1(2H)-thiones disclosed herein may be oxidized to the corresponding 7,7-dioxide compounds.

EXAMPLE 21

Substitution of an equivalent amount of a compound listed below:
methyl iodide
propyl iodide
butyl iodide
benzyl bromide
(2-bromoethyl)benzene
(3-bromopropyl)benzene
(4-bromobutyl)benzene
in the procedure of Example 3 for ethyl iodide gives the following compounds of this invention, respectively:

2-methyl-10-trifluoromethyl-1H-pyrimido[5,4,3-kl]phenothiazine-1,3(2H)-dione 2-propyl-10-trifluoromethyl-1H-pyrimido[5,4,3-kl]phenothiazine-1,3(2H)-dione 2-butyl-10-trifluoromethyl-1H-pyrimido[5,4,3-kl]phenothiazine-1,3(2H)-dione 2-benzyl-10-trifluoromethyl-1H-pyrimido[5,4,3-kl]phenothiazine-1,3(2H)-dione 2-(2-phenylethyl)-10-trifluoromethyl-1H-pyrimido[5,4,3-kl]phenothiazine-1,3(2H)-dione 2-(3-phenylpropyl)-10-trifluoromethyl-1H-pyrimido[5,4,3-kl]phenothiazine-1,3(2H)-dione 2-(4-phenylbutyl)-10-trifluoromethyl-1H-pyrimido[5,4,3-kl]phenothiazine-1,3(2H)-dione.

Similarly, the other pyrimido[5,4,3-kl]phenothiazine-1,3(2H)-diones and pyrimido[5,4,3-kl]phenothiazine-3-one-1(2H)-thiones disclosed herein may be alkylated with an alkyl or phenylalkyl halide listed above.

EXAMPLE 22

When 3-bromo-1-propanol, 4-bromobutanol or 1-bromo2-butanol is substituted in the procedure of Example 4 for 2-bromoethanol, the following compounds of this invention are obtained:

2-(3-hydroxypropyl)-10-trifluoromethyl-1H-pyrimido[5,4,3-kl]phenothiazine-1,3(2H)-dione 2-(4-hydroxybutyl)-10-trifluoromethyl-1H-pyrimido[5,4,3-kl]phenothiazine-1,3(2H)-dione 2-(2-hydroxybutyl)-10-trifluoromethyl-1H-pyrimido[5,4,3-kl]phenothiazine-1,3(2H)-dione.

In like manner, the other pyrimido[5,4,3-kl]phenothiazine-1,3(2H)-diones and pyrimido[5,4,3-kl]phenothiazine3-one-1(2H)-thiones disclosed herein may be alkylated with a hydroxyalkyl halide listed above.

EXAMPLE 23

Substitution of a dihydroxyalkyl halide listed below:
1-chloro-1,2-ethanediol
4-bromo-1,2-butanediol
4-bromo-1,3-butanediol
in the procedure of Example 5 for 3-chloro-1,2-dihydroxypropane gives the following diacetoxy compounds:
1-chloro-1,2-diacetoxyethane
4-bromo-1,2-diacetoxybutane
4-bromo-1,3-diacetoxybutane.

When a diacetoxy compound from above is reacted with 10-trifluoromethyl-1H-pyrimido[5,4,3-kl]phenothiazine1,3(2H)-dione as described in Example 5 and the product formed is hydrolyzed as described therein, the following compounds of this invention are obtained:

2-(1,2-dihydroxyethyl)-10-trifluoromethyl-1H-pyrimido[5,4,3-kl]phenothiazine-1,3(2H)-dione 2-(3,4-dihydroxybutyl)-10-trifluoromethyl-1H-pyrimido[5,4,3-kl]phenothiazine-1,3(2H)-dione 2-(2,4-dihydroxybutyl)-10-trifluoromethyl-1H-pyrimido[5,4,3-kl]phenothiazine-1,3(2H)-dione.

Similarly, the other pyrimido[5,4,3-kl]phenothiazine-1,3(2H)-diones and pyrimido[5,4,3-kl]phenothiazine-3-one-1(2H)-thiones disclosed herein may be alkylated with a diacetoxyalkyl halide listed above and the product thus formed subsequently hydrolyzed to the corresponding dihydroxylalkyl compound.

EXAMPLE 24

10-Propyl-1H-pyrimido[5,4,3-kl]phenothiazine-3-one-1(2H)-thione

A mixture of 11.7 g. (0.07 mol.) of 2-amino-4-propylbenzenethiol, 17.4 g. (0.07 mol.) of 2-bromo-3-nitrobenzoic acid, 38.7 g. (0.28 mol.) of anhydrous potassium carbonate and 6 g. (0.03 mol.) of sodium hydrosulfite in 125 ml. of dimethylformamide is stirred and heated for two hours at 125°–130°. The reaction mixture is cooled and stirred into 1000 ml. of dilute acetic acid. The solid that separates is collected, washed with water and dried to give 8-propylphenothiazine-1-carboxylic acid.

Use of 8-propylphenothiazine-1-carboxylic acid as a starting material in the procedure of Example 1 in place of 8-trifluoromethylphenothiazine-1-carboxylic acid gives the title compound as the final product.

EXAMPLE 25

10-Propyl-1H-pyrimido[5,4,3-kl]phenothiazine-1,3(2H)-dione

When 10-propyl-1H-pyrimido[5,4,3-kl]phenothiazine-3-one-1(2H)-thione is used in place of 10-trifluoromethyl-1H-pyrimido[5,4,3-kl]phenothiazine-3-one-1(2H)-thione in the procedure of Example 2, 1-methylmercapto-10-propyl-3H-pyrimido[5,4,3-kl]phenothiazine-3-one is obtained.

Hydrolysis of the 1-methylmercapto derivative as described in Example 2 gives the title compound.

EXAMPLE 26

2-(2-Hydroxyethyl)-10-propyl-1H-pyrimido[5,4,3-kl]phenothiazine-1,3(2H)-dione

Alkylation of 10-trifluoromethyl-1H-pyrimido[5,4,3-kl]phenothiazine-1,3(2H)-dione with 2-bromoethanol as described in the procedure of Example 4 gives the title compound.

EXAMPLE 27

Substitution of an equivalent amount of a benzenethiol listed below:
2-amino-5-ethoxybenzenethiol
2-amino-5-bromobenzenethiol
2-amino-5-nitrobenzenethiol
as a starting material in the procedure of Example 24 for 2-amino-4-propylbenzenethiol gives the following phenothiazine carboxylic acids as products:
7-ethoxyphenothiazine-1carboxylic acid
7-bromophenothiazine-1-carboxylic acid
7-nitrophenothiazine-1-carboxylic acid.

Use of a phenothiazine carboxylic acid listed above as a starting material in the procedure of Example 1 in place of 8-trifluoromethylphenothiazine-1-carboxylic acid gives the compounds of this invention listed below:
9-ethoxy-1H-pyrimido[5,4,3-kl]phenothiazine-1,3-(2H)-dione
9-bromo-1H-pyrimido[5,4,3-kl]phenothiazine-1,3-(2H)-dione
9-nitro-1H-pyrimido[5,4,3-kl]phenothiazine-1,3(2H)-dione.

EXAMPLE 28

Alkylation of a phenothiazine-1,3(2H)-dione listed in Example 27 with 2-bromoethanol according to the procedure of Example 4 gives the following compounds of this invention, respectively:
2-(2-hydroxyethyl)-9-ethoxy-1H-pyrimido[5,4,3-kl]phenothiazine-1,3(2H)-dione 1 2-(2-hydroxyethyl)-9-bromo-1H-pyrimido[5,4,3-kl]phenothiazine-1,3(2H)-dione
2-(2-hydroxyethyl)-9-nitro-1H-pyrimido[5,4,3-kl]phenothiazine-1,3(2H)-dione.

EXAMPLE 29

| Ingredients | Mg./Tablet |
| --- | --- |
| 2-(2-Hydroxyethyl)-10-trifluoromethyl-1H-pyrimido[5,4,3-kl]-phenothiazine-1,3(2H)-dione | 10 |
| Calcium sulfate, dihydrate | 150 |
| Sucrose | 25 |
| Starch | 15 |
| Talc | 5 |
| Stearic acid | 3 |

The sucrose, calcium sulfate and 2-(2-hydroxyethyl)-10trifluoromethyl-1H-pyrimido[5,4,3-kl]phenothiazine-1,3(2H)-dione are thoroughly mixed and granulated with hot 10% gelatin solution. The wetted mass is passed through a No. 6 mesh screen directly onto drying trays. The granules are dried at 120°F. and passed through a No. 20 mesh screen, mixed with the starch, talc and stearic acid and compressed into tablets.

In a similar manner, the other compounds of this invention disclosed herein may be formulated into tablets.

What is claimed is:
1. A compound of the formula:

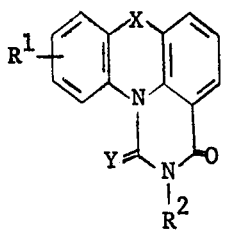

in which:
X is S, SO or $SO_2$;
Y is O or S;
$R^1$ is hydrogen, halogen, lower alkyl, lower alkoxy, trifluoromethyl or nitro; and
$R^2$ is hydrogen, lower alkyl, hydroxy(lower)alkyl, dihydroxy(lower)alkyl or phenyl(lower)alkyl.

2. A compound according to claim 1 in which Y is S.
3. A compound according to claim 1 in which Y is O.
4. A compound according to claim 3 in which $R^1$ is in the 10-position and $R^2$ is hydrogen, lower alkyl or hydroxy(lower)alkyl.
5. A compound according to claim 4 in which $R^1$ is trifluoromethyl in the 10-position and X is SO or $SO_2$.
6. A compound according to claim 5, said compound being 2-(2-hydroxyethyl)-10-trifluoromethyl-1H-pyrimido[5,4,3-kl]phenothiazine-1,3(2H)-dione-7-oxide.
7. A compound according to claim 5, said compound being 2-(2-hydroxyethyl)-10-trifluoromethyl-1H-pyrimido[5,4,3-kl]phenothiazine-1,3(2H)-dione-7,7-dioxide.
8. A compound according to claim 5, said compound being 2-ethyl-10-trifluoromethyl-1H-pyrimido[5,4,3-kl]phenothiazine-1,3(2H)-dione-7-oxide.
9. A compound according to claim 5, said compound being 10-trifluoromethyl-1H-pyrimido[5,4,3-kl]phenothiazine1,3(2H)-dione-7,7-dioxide.
10. A compound according to claim 5, said compound being 10-trifluoromethyl-1H-pyrimido[5,4,3-kl]phenothiazine1,3(2H)-dione-7-oxide.
11. A pharmaceutical composition having antiarthritic activity, in dosage unit form, comprising a pharmaceutical carrier and an effective but nontoxic amount of a compound as claimed in claim 1.
12. A method of treating arthritis which comprises administering internally to an animal subject an amount of a compound as claimed in claim 1 sufficient to inhibit arthritis.

* * * * *

UNITED STATES PATENT OFFICE
CERTIFICATE OF CORRECTION

PATENT NO. : 3,962,438
DATED : June 8, 1976
INVENTOR(S) : Charles E. Berkoff, Blaine M. Sutton and Joseph Weinstock It is certified that error appears in the above-identified patent and that said Letters Patent are hereby corrected as shown below:

Column 3, line 17, the second "$R^1$" should read --R'--

Column 3, line 70, "hing" should read --hind--

Column 7, line 41, "2-ethyl10-" should read --2-ethyl-10- --

Column 8, line 28, "2ethyl10-" should read --2-ethyl-10- --

Column 8, line 50, "(2,3di" should read --(2,3-di--

Column 8, line 54, "1-chlorobutanemethanol" should read
--1-chlorobutane-methanol--

Column 11, line 18, "bromo2-" should read --bromo-2- --

Column 12, lines 64-66, should read as follows:
kl]phenothiazine-1,3(2H)-dione
2-(2-hydroxyethyl)-9-bromo-1H-pyrimido[5,4,3-
kl]phenothiazine-1,3(2H)-dione Column 13, line 14, "10trifluoromethyl-" should read --10-tri-
fluoromethyl- --

Column 14, Claim 9, line 27, "thiazinel,3(2H)-" should
read --thiazine-1,3(2H)- --

Column 14, Claim 10, line 29, "kl]phenothiazinel,3(2H)-"
should read --kl]phenothiazine-1,3(2H)- --

Signed and Sealed this

Seventh Day of September 1976

[SEAL]

Attest:

RUTH C. MASON
Attesting Officer

C. MARSHALL DANN
Commissioner of Patents and Trademarks